(12) United States Patent
Ohnishi et al.

(10) Patent No.: US 10,717,217 B2
(45) Date of Patent: Jul. 21, 2020

(54) TUBE, METHOD FOR PRODUCING TUBE, AND MOLD

(71) Applicant: TATSUTA ELECTRIC WIRE & CABLE CO., LTD., Osaka (JP)

(72) Inventors: Hisafumi Ohnishi, Osaka (JP); Shinji Yoshino, Kyoto (JP); Yoshio Hirano, Kyoto (JP)

(73) Assignee: TATSUTA ELECTRIC WIRE & CABLE CO., LTD., Osaka (JP)

( * ) Notice: Subject to any disclaimer, the term of this patent is extended or adjusted under 35 U.S.C. 154(b) by 327 days.

(21) Appl. No.: 15/116,387

(22) PCT Filed: Feb. 4, 2015

(86) PCT No.: PCT/JP2015/053081
§ 371 (c)(1),
(2) Date: Aug. 3, 2016

(87) PCT Pub. No.: WO2015/119142
PCT Pub. Date: Aug. 13, 2015

(65) Prior Publication Data
US 2017/0008209 A1  Jan. 12, 2017

(30) Foreign Application Priority Data

Feb. 7, 2014 (JP) .................................. 2014-022671

(51) Int. Cl.
*B29C 45/16* (2006.01)
*B32B 27/08* (2006.01)
(Continued)

(52) U.S. Cl.
CPC ......... *B29C 45/1671* (2013.01); *A61M 39/08* (2013.01); *B29C 45/1615* (2013.01);
(Continued)

(58) Field of Classification Search
CPC .... B29C 2045/1617; B29C 2045/1673; B29C 45/1615; B29C 45/1671; B29C 45/2602;
(Continued)

(56) References Cited

U.S. PATENT DOCUMENTS 4,174,367 A 11/1979 Breher
4,652,475 A 3/1987 Haney et al.
(Continued)

FOREIGN PATENT DOCUMENTS

CN 101691897 A 4/2010
JP 04-174663 A 6/1992
(Continued)

OTHER PUBLICATIONS

Extended European Search Report for EP patent application No. 157458324 (dated Aug. 31, 2017).
(Continued)

*Primary Examiner* — Yan Lan
(74) *Attorney, Agent, or Firm* — Mintz Levin Cohn Ferris Glovsky and Popeo, P.C.; David G. Conlin; Steven M. Jensen

(57) ABSTRACT

The present invention molds, with simple processes, a tube which has a smaller outer diameter and is hardly bent in a folded manner. The present invention includes (i) a primary molding step of forming a primary molded body by carrying out resin molding while a reinforcing member and a core pin (4) are placed in a cavity of a first mold made up of a lower mold (30) and an upper mold (40) for primary molding and (ii) a secondary molding step of covering the reinforcing member by carrying out resin molding while the primary molded body is placed in a cavity of a second mold that has an inner diameter larger than an inner diameter of the cavity of the first mold.

2 Claims, 7 Drawing Sheets

(51) Int. Cl.
  *B29C 45/26* (2006.01)
  *A61M 39/08* (2006.01)
  *B29L 31/00* (2006.01)
  *B29C 45/37* (2006.01)
  *B29L 23/00* (2006.01)
  *B29K 101/12* (2006.01)
  *B29K 105/00* (2006.01)

(52) U.S. Cl.
  CPC .......... *B29C 45/2602* (2013.01); *B32B 27/08* (2013.01); *B29C 45/261* (2013.01); *B29C 45/37* (2013.01); *B29C 2045/1617* (2013.01); *B29C 2045/1673* (2013.01); *B29K 2101/12* (2013.01); *B29K 2105/0067* (2013.01); *B29L 2023/22* (2013.01); *B29L 2031/753* (2013.01); *B29L 2031/7542* (2013.01); *B32B 2535/00* (2013.01)

(58) Field of Classification Search
  CPC ...... B29C 45/261; B29C 45/37; A61M 39/08; B29K 2101/12; B29K 2105/0067; B29L 2023/22; B29L 2031/753; B29L 2031/7542; B32B 2535/00; B32B 27/08
  See application file for complete search history.

(56) References Cited

U.S. PATENT DOCUMENTS

| | | | |
|---|---|---|---|
| 5,245,955 A | | 9/1993 | Husted |
| 5,935,122 A | * | 8/1999 | Fourkas ............... A61M 25/005 604/249 |
| 5,951,539 A | * | 9/1999 | Nita ................... A61M 25/0053 604/524 |
| 2003/0015816 A1 | | 1/2003 | Rapacki et al. |

FOREIGN PATENT DOCUMENTS

| | | |
|---|---|---|
| JP | 2005-256934 A | 9/2005 |
| JP | 2007-136713 A | 6/2007 |
| JP | 2008-252666 A | 10/2008 |
| JP | 2010-048333 A | 3/2010 |
| JP | 2013-180545 A | 9/2013 |

OTHER PUBLICATIONS

Extended European Search Report for EP patent application No. 15746251.6 (dated Aug. 31, 2017).
Chinese Office action issued in Chinese Patent Application No. 201580007272.7 dated Jan. 8, 2018.
International Preliminary Report on Patentability for PCT/JP2015/053081 (dated Aug. 18, 2016).
International Search Report for PCT/JP2015/053081 (dated Apr. 21, 2015).
International Preliminary Report on Patentability for PCT/JP2015/053082 (dated Aug. 18, 2016).
International Search Report for PCT/JP2015/053082 (dated Apr. 21, 2015).
Office Action issued in co-pending U.S. Appl. No. 15/116,506 dated Oct. 29, 2018.
Final Office Action dated Jun. 3, 2019 in co-pending U.S. Appl. No. 15/116,506.
Office Action/restriction requirement issued in co-pending U.S. Appl. No. 15/116,506 dated Aug. 2, 2018.

\* cited by examiner (a)

(b)

(c)

(d)

(e)

(a)

(b)

(c)

(d)

(a)

(b)

(c)

(d)

(a)

(b)

(c)

(d)

TUBE, METHOD FOR PRODUCING TUBE, AND MOLD

CROSS-REFERENCE TO RELATED APPLICATIONS

This application is a National Phase application filed under 35 USC 371 of PCT International Application No. PCT/JP2015/053081 with an International Filing Date of Feb. 4, 2015, which claims under 35 U.S.C. § 119(a) the benefit of Japanese Application No. 2014-022671, filed Feb. 7, 2014, the entire contents of which are incorporated herein by reference.

TECHNICAL FIELD

The present invention relates to a tube, a method for producing a tube, and a mold.

BACKGROUND ART

As one of medical instruments, a cannula which is a tubular component is known. In general, the cannula is made of resin and is inserted into a lumen, a blood vessel, or the like of a patient for excreting a body fluid or for instillation of a drug solution, a contrast medium, or the like.

Examples of a method for molding a medical tube (such as a cannula) which is made of resin encompass molding methods such as extrusion molding and injection molding. Patent Literature 1 discloses a method for producing a medical tube by injection molding.

In a case where a medical tube is molded by injection molding, it is possible to collectively form, in an injection molding step, another member to be attached to the medical tube, and this brings an advantage of simplifying production processes. Furthermore, the injection molding has an advantage that a tube which has a complicated shape and is difficult to produce by extrusion molding can be produced with high accuracy.

A medical tube which is made of only resin is bent in a folded manner by applied force, and a hollow section at the bent part becomes narrower. This disturbs transfer of blood, a drug solution, or the like and may cause a problem that such a liquid cannot be transferred at all depending on circumstances.

In order to solve the problem, in the medical tube of Patent Literature 1, a reinforcing body having a spiral shape is embedded in a thick wall part (wall section). This makes it possible to cause the medical tube to be hardly bent in a folded manner and consequently to restrain the hollow section from being narrowed, and further to prevent the disturbance in transfer of a drug or the like.

A method of Patent Literature 1 for producing a medical tube is a production method in which (i) firstly a core pin is covered with a silicone rubber tube which has been molded in advance, (ii) secondly the silicone rubber tube is covered with a reinforcing body which is made of stainless steel and has a spiral shape, and (iii) thirdly the core pin covered with the reinforcing body and the silicone rubber tube is set in a cavity of a mold and injection molding is carried out. By the production method, a tube can be produced in which the reinforcing body having the spiral shape is embedded in a wall section.

Moreover, Patent Literature 2 discloses a production method in which (i) a primary molded body corresponding to a lower-half part of a tube is molded with use of a mold for first molding and a mold for closing and (ii) a secondary molded body corresponding to an upper-half part of the tube is molded with use of a mold for second molding instead of the mold for closing. With the production method, a tube having a thin wall can be molded with high accuracy.

CITATION LIST

Patent Literature

[Patent Literature 1]
Japanese Patent Application Publication Tokukaihei No. 4-174663 (Publication date: Jun. 22, 1992)
[Patent Literature 2]
Japanese Patent Application Publication Tokukai No. 2013-180545 (Publication date: Sep. 12, 2013)
[Patent Literature 3]
Japanese Patent Application Publication Tokukai No. 2007-136713 (Publication date: Jun. 7, 2007)

SUMMARY OF INVENTION

Technical Problem

However, in the production method of Patent Literature 1, the silicone rubber tube is prepared in advance, the silicone rubber tube is covered with the reinforcing body having a spiral shape, and further the injection molding is carried out. As such, the processes are complicated as compared with processes for producing a tube having no reinforcing body.

Moreover, in the production method of Patent Literature 1, the silicone rubber tube is covered with the reinforcing body, and therefore the reinforcing body is designed to have an inner diameter which is larger than an outer diameter of the silicone rubber tube. This causes a problem that it is difficult to control arrangement of the reinforcing body so that a central axis of the silicone rubber tube conforms to a central axis of the reinforcing body. From this, the reinforcing body may deviate in position in the wall section of the obtained medical tube in a radial direction of the medical tube (i.e., in a direction perpendicular to a longitudinal direction of the medical tube). Further, the reinforcing body may be partially exposed in a surface of the tube, depending on circumstances.

In order to surely embed the reinforcing body in the wall section so that the reinforcing body is not exposed, it is necessary to design the wall section to be thick in advance so as to prevent the reinforcing body from being exposed even in a case where thickness deviation occurs in the wall section when the injection molding is carried out. As a result, an outer diameter of the medical tube becomes larger than necessary with respect to an inner diameter, and this increases a burden to a patient.

Further, in a case where a gap between the silicone rubber tube and the reinforcing body is large in a state in which the silicone rubber tube is covered with the reinforcing body, the reinforcing body is moved from a predetermined position by pressure applied to the reinforcing body in the injection molding. In particular, the reinforcing body is moved in a longitudinal direction of the silicone rubber tube by injection pressure and accordingly deviates from the predetermined position.

In view of this, in order to reduce a gap between the silicone rubber tube and the reinforcing body, it may be considered that the reinforcing body is designed to have an inner diameter which is less different from an outer diameter of the silicone rubber tube. However, in a case where the reinforcing body and the silicone rubber tube are designed as above described, it becomes difficult to put the reinforcing body over a surface of the silicone rubber tube at a predetermined position, and this leads to a problem of taking time to carry out this step.

Moreover, the production method of Patent Literature 2 is a complicated production method which (i) includes the step of molding the lower-half part of the tube and the step of molding the upper-half part of the tube and, further, (ii) requires three kinds of molds. In a case where a tube in which a reinforcing body is embedded in a wall section is produced by using the production method of Patent Literature 2, processes become further complicated, and the number of required molds further increases.

The present invention is accomplished in view of the problems, and its object is to provide (i) a tube which has a small outer diameter and is hardly bent in a folded manner, (ii) a tube production method for molding the tube with simple processes, and (iii) a mold for use in molding of the tube.

Solution to Problem

In order to attain the object, a tube production method in accordance with an aspect of the present invention is a method for producing a tube which includes a wall section, a hollow section, and a reinforcing member, the reinforcing member being provided in the wall section and having a ring shape, a wide-ring shape, or a spiral shape, the method including the steps of: (a) forming a primary molded body, in which the reinforcing member is provided along an outer peripheral surface of a tubular resin, by carrying out resin molding while the reinforcing member and a core pin for forming the hollow section are placed in a cavity of a first mold; and (b) covering the reinforcing member by carrying out resin molding while the primary molded body is placed in a cavity of a second mold which has an inner diameter larger than an inner diameter of the first mold.

Moreover, in order to attain the object, a mold in accordance with an aspect of the present invention is a mold for forming a tube which includes a wall section, a hollow section, and a reinforcing member, the reinforcing member being provided in the wall section and having a ring shape, a wide-ring shape, or a spiral shape, the mold including: a groove corresponding to a shape of the reinforcing member, the groove being provided in an inner wall surface that forms a cavity.

Moreover, in order to attain the object, the tube in accordance with an aspect of the present invention is a tube including: a wall section; a hollow section; a reinforcing member which is provided in the wall section and serves as at least one ring-shaped member, at least one wide-ring-shaped member, or at least one turn of a spiral-shaped member; a first resin layer; and a second resin layer which is provided on an outer side of the first resin layer, in a cross section of the tube taken along a plane including an axis direction of the tube, a cross section of the reinforcing member being located in a boundary between the first resin layer and the second resin layer, a part of the first resin layer, which part is around the cross section of the reinforcing member, being thicker than other parts of the first resin layer, and a part of the second resin layer, which part is around the cross section of the reinforcing member, being thinner than other parts of the second resin layer.

Note that, in the present invention, the term "mold" means a "mold" used in resin molding, and a material of the mold can be selected as appropriate from metal materials and nonmetal materials in accordance with a resin molding method.

Advantageous Effects of Invention

According to an aspect of the present invention, it is possible to provide (i) a tube which has a thin wall section and is hardly bent in a folded manner, (ii) a tube production method for molding the tube with simple processes, and (iii) a mold for use in molding of the tube.

DESCRIPTION OF EMBODIMENTS

Embodiment 1

The following description will discuss, with reference to FIGS. 1 through 5, details of a method for producing a tube, a tube, and a mold in accordance with an embodiment of the present invention.

<Resin Molding Mold>

Figure 1:
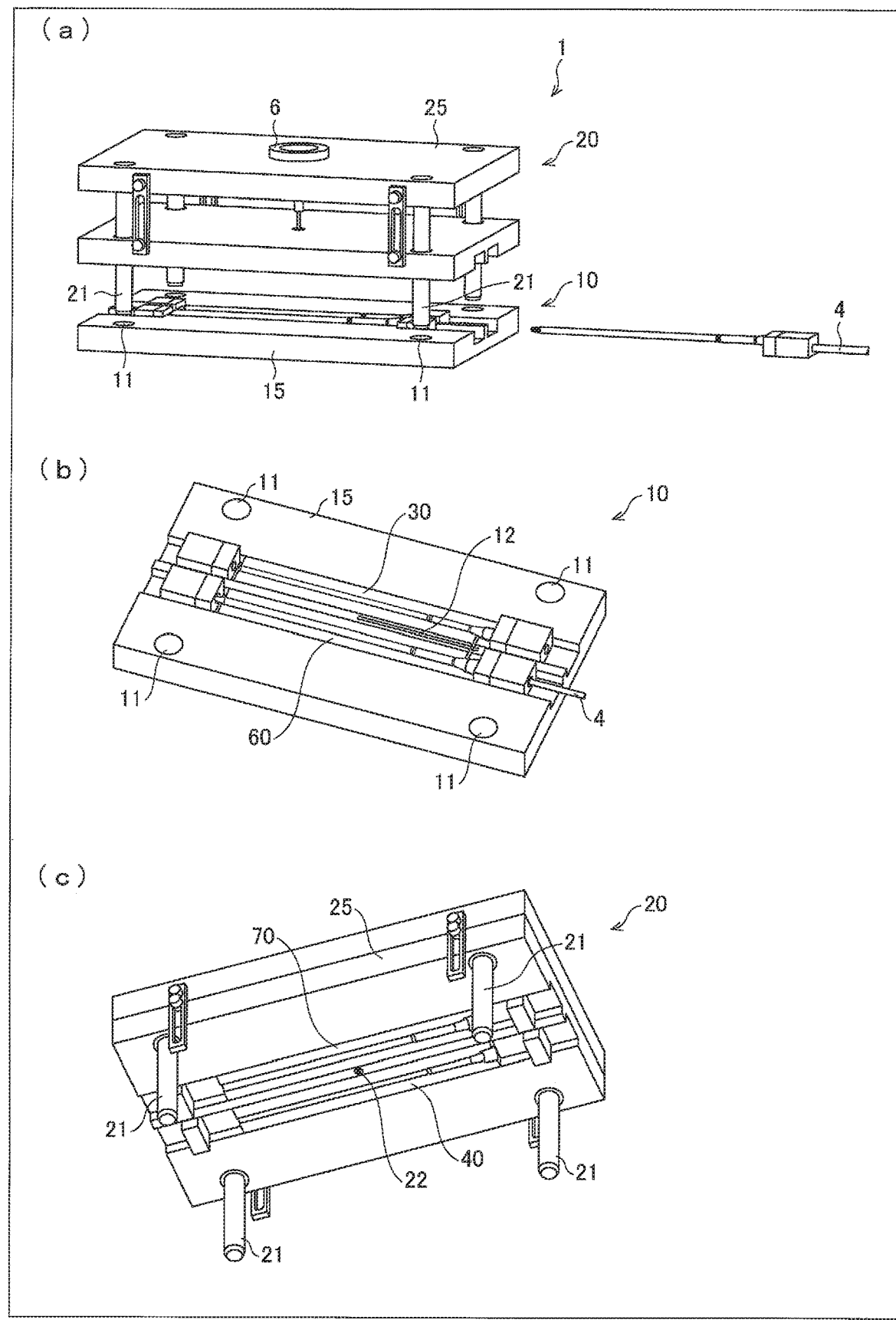
FIG. 1 is a perspective view partially illustrating a resin molding mold in accordance with Embodiment 1 of the present invention. (a) of FIG. 1 illustrates a state where a resin receiving side mold and an opposite side mold face each other, (b) of FIG. 1 illustrates the opposite side mold, and (c) of FIG. 1 illustrates the resin receiving side mold.

FIG. 1 is a perspective view partially illustrating a resin molding mold 1 in accordance with Embodiment 1. (a) of FIG. 1 illustrates a state where a resin receiving side mold and an opposite side mold face each other, (b) of FIG. 1 illustrates the opposite side mold, and (c) of FIG. 1 illustrates the resin receiving side mold.

Examples of resin molding which can be employed in the present invention encompass injection molding, vacuum injection, and the like. In the following descriptions, an embodiment of injection molding is first described, and an embodiment of vacuum injection will be described later.

An injection molding machine includes a resin molding mold 1 and an injection unit (not illustrated). The injection unit has a configuration which is identical with that of a conventional injection unit, and is therefore not illustrated in a drawing and not described in detail.

As illustrated in (a) of FIG. 1, the resin molding mold 1 includes an opposite side mold 10 and a resin receiving side mold 20 which are arranged so as to face each other. In a case of injection molding, the resin receiving side mold is sometimes referred to as an injection-side mold. Moreover, as illustrated in (b) of FIG. 1, the opposite side mold 10 includes an opposite side mold plate 15, and a lower mold 30 for primary molding and a lower mold 60 for secondary molding which are provide on the opposite side mold plate 15. Further, as illustrated in (c) of FIG. 1, the resin receiving side mold 20 includes a resin receiving side mounting plate 25 (base plate), and an upper mold 40 for primary molding and an upper mold 70 for secondary molding which are provided on the resin receiving side mounting plate 25.

As illustrated in (a) and (c) of FIG. 1, the resin receiving side mounting plate 25 is provided with (i) a locate ring 6 for making alignment with the injection unit easy and (ii) four guide pins 21 which are provided at respective four corners of a surface facing the opposite side mold 10. Moreover, as illustrated in (b) of FIG. 1, the opposite side mold plate 15 has guide pin bushes 11 into which the guide pins 21 are to be respectively inserted. By inserting the guide pins 21 into the respective guide pin bushes 11, the resin receiving side mold 20 and the opposite side mold 10 are closely brought into contact while being aligned with each other. As such, clamping of the resin molding mold 1 is carried out.

As illustrated in (b) of FIG. 1, the opposite side mold 10 has a runner 12 which is provided on a surface facing the resin receiving side mold 20. Moreover, the resin receiving side mold 20 has a sprue 22 which is to communicate with the runner 12 when the resin molding mold 1 is clamped. The sprue 22 passes through the resin receiving side mold 20, and molten resin is introduced from a nozzle of the injection unit via a sprue bush.

When the resin molding mold 1 is clamped, a first mold that is a mold for primary molding is formed by the lower mold 30 for primary molding and the upper mold 40 for primary molding, and a second mold for secondary molding is formed by the lower mold 60 for secondary molding and the upper mold 70 for secondary molding. Note that an inner diameter (i.e., a diameter of a cavity) of the second mold is larger than an inner diameter (i.e., a diameter of a cavity) of the first mold.

Figure 2:
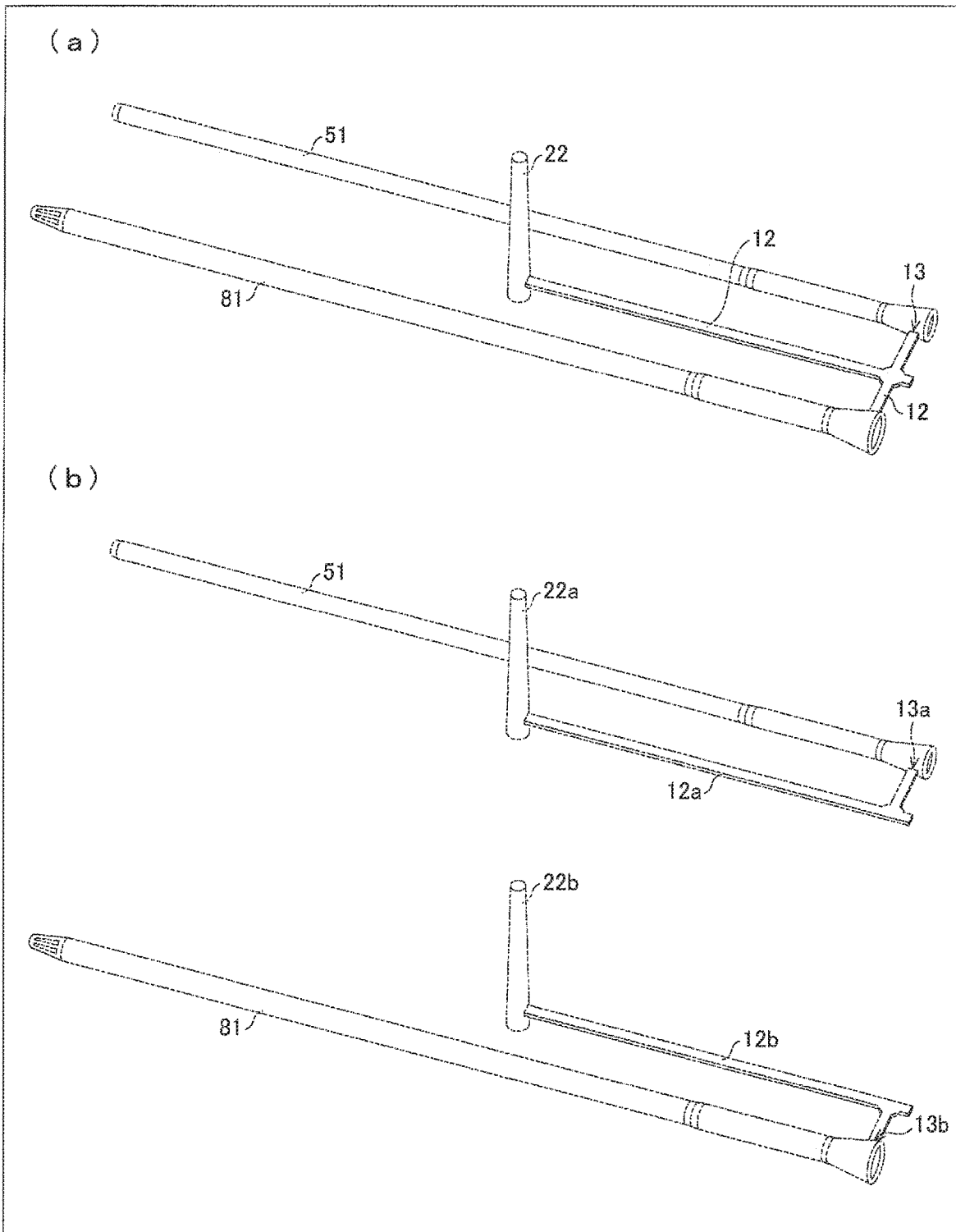
FIG. 2 is a virtual perspective view illustrating a path through which molten resin flows. (a) of FIG. 2 is a virtual perspective view illustrating a path through which molten resin flows in the mold in accordance with Embodiment 1, and (b) of FIG. 2 is a virtual perspective view illustrating a path through which molten resin flows in a mold in accordance with a modification example.

FIG. 2 is a virtual perspective view illustrating a path through which molten resin flows. (a) of FIG. 2 is a virtual perspective view illustrating a path through which molten resin flows in the mold in accordance with Embodiment 1, and (b) of FIG. 2 is a virtual perspective view illustrating a path through which molten resin flows in a mold in accordance with a modification example.

As illustrated in (a) of FIG. 2, the molten resin is introduced to a cavity 51 of the first mold and to a cavity 81 of the second mold via the sprue 22, the runner 12, and a gate 13. Each of the cavity 51 of the first mold and the cavity 81 of the second mold has a substantially cylindrical shape.

The resin molding mold 1 of Embodiment 1 has a configuration in which the runner 12 branches so that the molten resin is introduced to the cavity 51 of the first mold and to the cavity 81 of the second mold via the one (1) runner 12. Note, however, that Embodiment 1 is not limited to this and can employ a configuration in which the first mold and the second mold are separated from each other. That is, as illustrated in (b) of FIG. 2, it is possible to employ a configuration in which (i) molten resin is introduced to the cavity 51 of the first mold via a sprue 22*a* and a runner 12*a* which are provided for the first mold and (ii) molten resin is introduced to the cavity 81 of the second mold via a sprue 22*b* and a runner 12*b* which are provided for the second mold. Alternatively, the first mold can be a composite mold in which the runner 12*a* illustrated in (b) of FIG. 2 is caused to branch so that molten resin is introduced to a plurality of cavities 51 in the first mold. Similarly, the second mold can be a composite mold.

The resin molding mold 1 of Embodiment 1 includes the first mold and the second mold. Note, however, that Embodiment 1 is not limited to this and it is possible to employ a resin molding mold including only a first mold and a resin molding mold including only a second mold.

In a case where a tube having a hollow section is formed by resin molding, the resin molding is carried out in a state where a core pin 4 serving as a slide core is inserted in the cavity of the mold as illustrated in (a) of FIG. 1. The core pin 4 is inserted in the cavity so that a central axis of the core pin 4 conforms to a central axis of the cavity.

<Tube>

Figure 3:
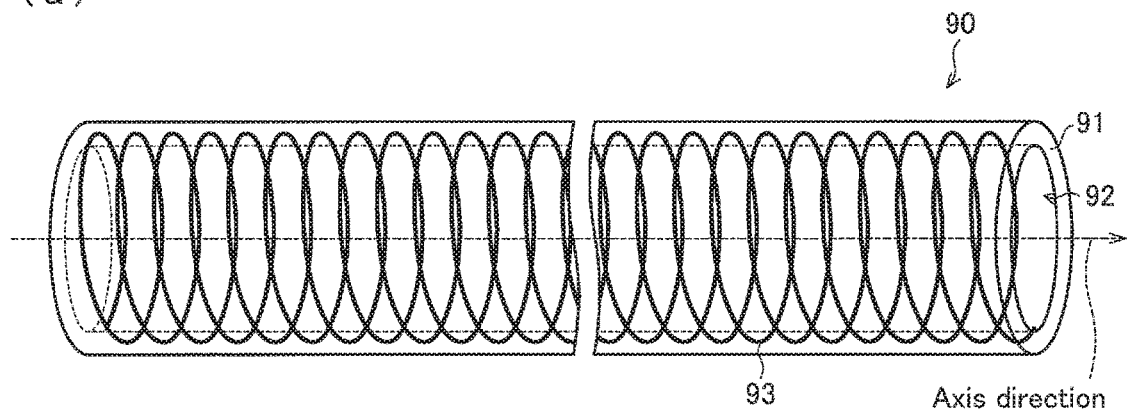
FIG. 3 is a view schematically illustrating a tube in accordance with Embodiment 1 of the present invention. (a) of FIG. 3 is a perspective view, (b) of FIG. 3 is a partial lateral view, (c) of FIG. 3 is a cross-sectional view taken along the line a-a in (b) of FIG. 3, and each of (d) and (e) of FIG. 3 is a partial cross-sectional view taken along the line b-b in (c) of FIG. 3.
Figure 3:
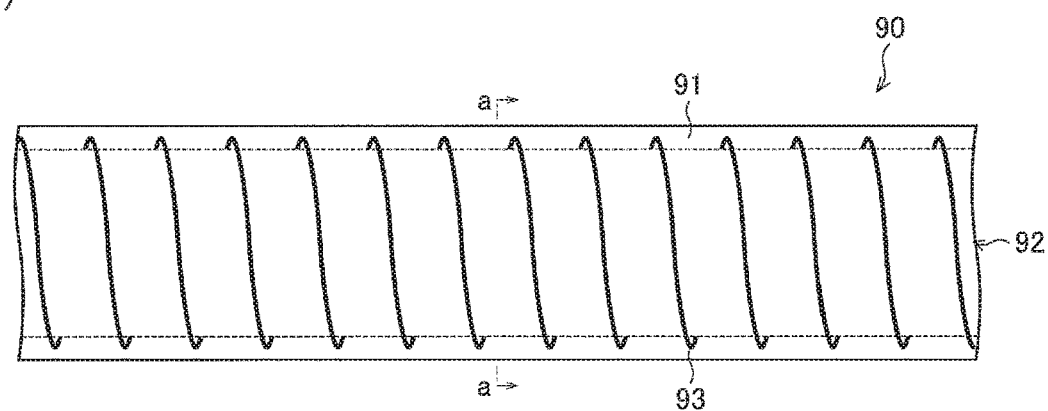
Figure 3:
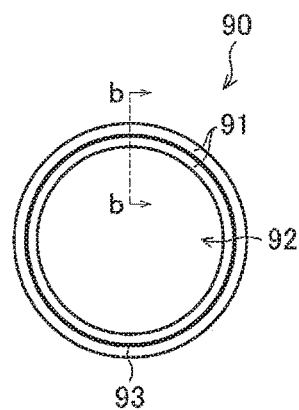
Figure 3:
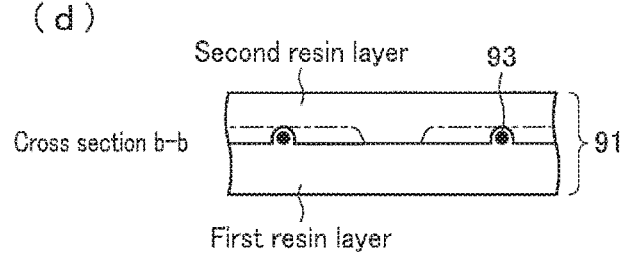
Figure 3:
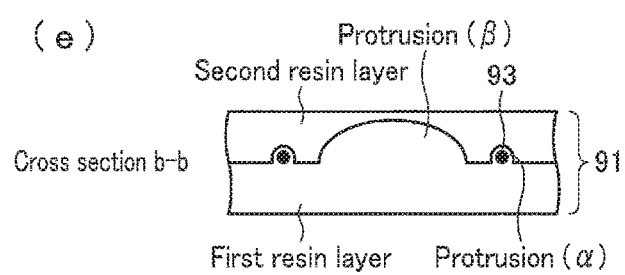

FIG. 3 is a view schematically illustrating a tube 90 in accordance with Embodiment 1. (a) of FIG. 3 is a perspective view, (b) of FIG. 3 is a partial lateral view, and (c) of FIG. 3 is a cross-sectional view taken along the line a-a in (b) of FIG. 3. The tube 90 has a wall section 91 and a hollow section 92, and a reinforcing member 93 is embedded in the wall section 91.

FIG. 3 exemplifies the tube 90 of Embodiment 1 in which the reinforcing member 93 that is a spiral-shaped member made up of a plurality of turns of spiral sections (i.e., a coil, a plate-like spring) is embedded in the wall section 91. Note, however, that Embodiment 1 is not limited to this. The tube 90 of Embodiment 1 can be a tube in which a reinforcing member that is (i) a spiral-shaped member made up of at least one turn of a spiral section or (ii) at least one ring-shaped member (which can be a ring or a wide-ring-shaped member) is embedded in a part to be reinforced. Alternatively, the tube 90 can be a tube in which an embedded reinforcing member is a plurality of ring-shaped members which are arranged in an axis direction of the tube 90 at predetermined intervals similar to those of the above plurality of turns of spiral sections serving as the reinforcing member 93. Alternatively, the reinforcing member can be a member formed by combining a spiral-shaped member and a ring-shaped member.

The tube 90 includes the reinforcing member 93, and therefore the tube 90 is hardly bent in a folded manner and it is consequently possible to prevent the hollow section 92 from becoming narrow even in a case where external force is applied to the tube 90.

<Mold>

Figure 4:
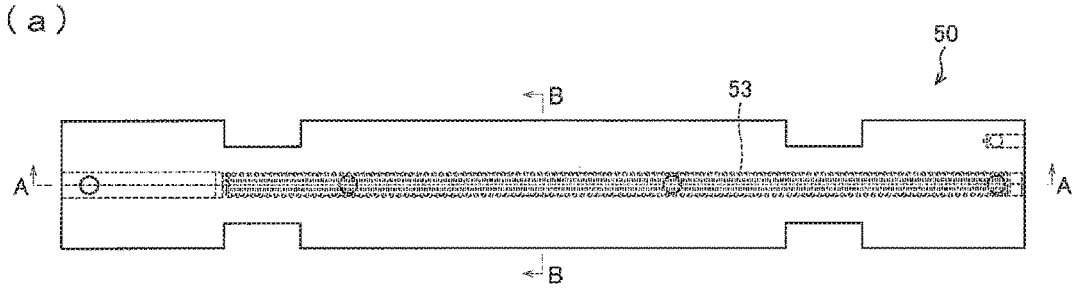
FIG. 4 is a view schematically illustrating a first mold in accordance with Embodiment 1 of the present invention. (a) of FIG. 4 is a plan view, (b) of FIG. 4 is a cross-sectional view taken along the line A-A in (a) of FIG. 4, (c) of FIG. 4 is a cross-sectional view taken along the line B-B in (a) of FIG. 4, and (d) of FIG. 4 is an enlarged view illustrating a part C in (b) of FIG. 4.
Figure 4:
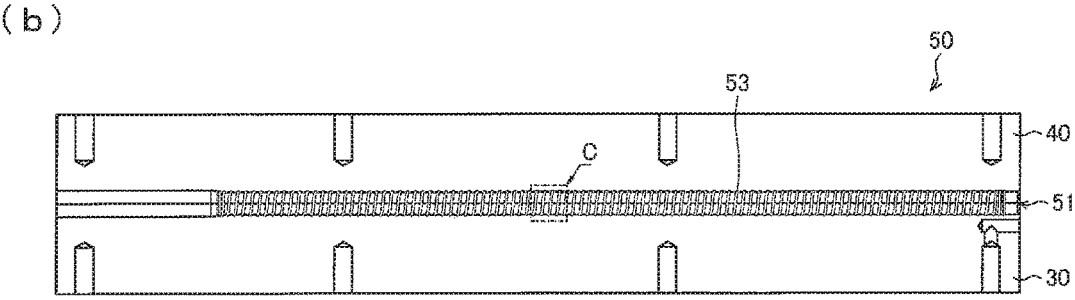
Figure 4:
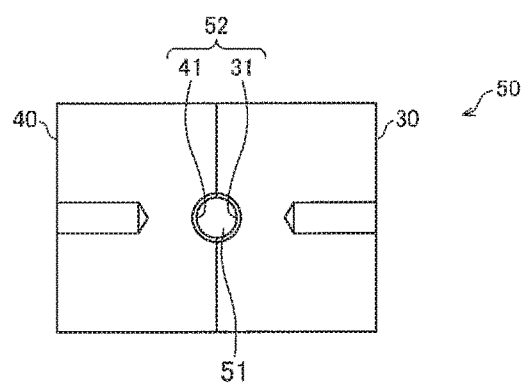
Figure 4:
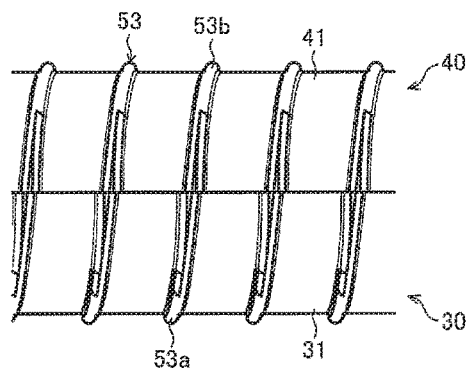
Figure 5:
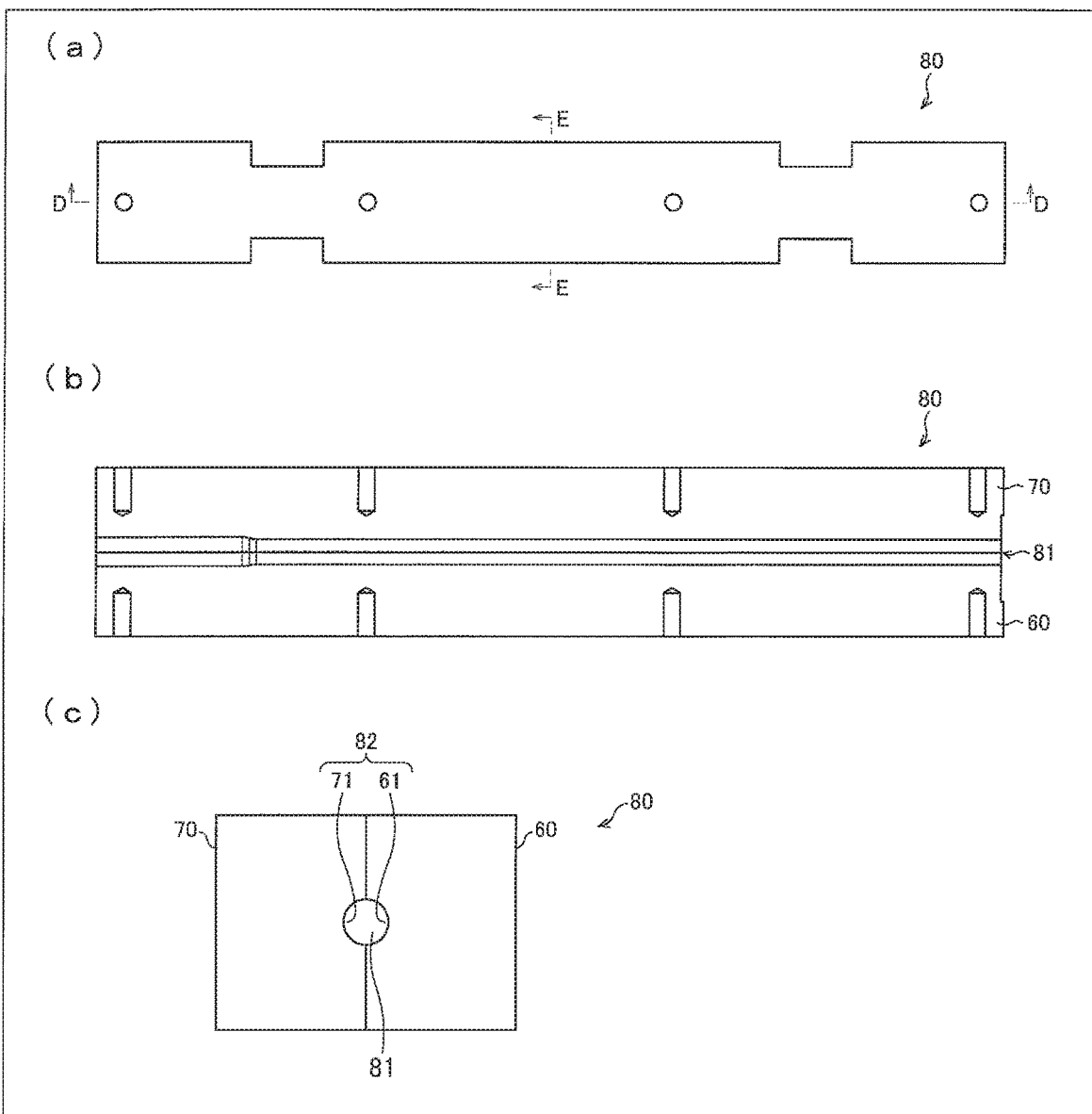
FIG. 5 is a view schematically illustrating a second mold in accordance with Embodiment 1 of the present invention. (a) of FIG. 5 is a plan view, (b) of FIG. 5 is a cross-sectional view taken along the line D-D in (a) of FIG. 5, and (c) of FIG. 5 is a cross-sectional view taken along the line E-E in (a) of FIG. 5.

The following description will discuss, with reference to FIGS. 4 and 5, the resin molding mold 1 which can be suitably used to produce the tube 90. The resin molding mold 1 of Embodiment 1 includes a first mold 50 and a second mold 80.

FIG. 4 is a view schematically illustrating the first mold 50 in accordance with Embodiment 1. (a) of FIG. 4 is a plan view, (b) of FIG. 4 is a cross-sectional view taken along the line A-A in (a) of FIG. 4, (c) of FIG. 4 is a cross-sectional view taken along the line B-B in (a) of FIG. 4, and (d) of FIG. 4 is an enlarged view illustrating a part C in (b) of FIG. 4. For explanation, (a) of FIG. 4 illustrates a groove which is provided in an inner wall surface of the first mold.

As illustrated in (c) of FIG. 4, the lower mold 30 for primary molding and the upper mold 40 for primary molding which constitute the first mold 50 are cavity type molds. By clamping the lower mold 30 for primary molding and the upper mold 40 for primary molding, the cavity 51 having a substantially cylindrical shape is formed as a hollow part in the first mold 50. Moreover, an inner wall surface 52 of the first mold 50 includes an inner wall surface 31 of the lower mold 30 for primary molding and an inner wall surface 41 of the upper mold 40 for primary molding.

In each of the inner wall surface 31 and the inner wall surface 41, a groove 53 corresponding to a shape of the reinforcing member 93 is provided. That is, as illustrated in (d) of FIG. 4, a groove 53a which is a part of the groove 53 is provided in the inner wall surface 31, and a groove 53b which is a part of the groove 53 is provided in the inner wall surface 41. When the lower mold 30 for primary molding and the upper mold 40 for primary molding are clamped, the grooves 53a and 53b which are respectively provided in the inner wall surface 31 and the inner wall surface 41 are combined into the groove 53 which is provided in the inner wall surface 52 of the first mold 50 and corresponds to a spiral shape of the reinforcing member 93. Note that, in a case where a tube is produced in which a reinforcing member having a ring shape is embedded in a wall section, it is possible to use, as the first mold 50 of the resin molding mold 1, a mold in which a ring-shaped groove is provided in the inner wall surface 52.

Here, FIG. 4 illustrates the example in which the groove has a spiral shape. Note, however, that Embodiment 1 is not limited to this and a shape of the groove can be changed as appropriate in accordance with a shape of the reinforcing member. For example, the groove can have a shape formed by a plurality of ring-shaped grooves or a plurality of wide-ring-shaped grooves which are arranged at regular intervals or at controlled irregular intervals in a direction parallel to a central axis of the cavity. Alternatively, the groove can have a shape formed by combining arbitrarily selected two or more of a spiral shape, a ring shape, and a wide-ring shape.

FIG. 5 is a view schematically illustrating the second mold 80 in accordance with Embodiment 1. (a) of FIG. 5 is a plan view, (b) of FIG. 5 is a cross-sectional view taken along the line D-D in (a) of FIG. 5, and (c) of FIG. 5 is a cross-sectional view taken along the line E-E in (a) of FIG. 5.

As illustrated in (c) of FIG. 5, the lower mold 60 for secondary molding and the upper mold 70 for secondary molding which constitute the second mold 80 are cavity type molds. By clamping the lower mold 60 for secondary molding and the upper mold 70 for secondary molding, the cavity 81 having a substantially cylindrical shape is formed as a hollow part in the second mold 80. Moreover, an inner wall surface 82 of the second mold 80 includes an inner wall surface 61 of the lower mold 60 for secondary molding and an inner wall surface 71 of the upper mold 70 for secondary molding.

A diameter of the cavity 81 in the second mold 80 is larger than a diameter of the cavity 51 in the first mold 50. That is, an inner diameter of the second mold 80 is larger than an inner diameter of the first mold 50. Note that the term "diameter" of the cavity 51 in the first mold 50 means a diameter of the cavity 51 including the groove 53. Specifically, the diameter of the cavity 51 in the first mold 50 means a diameter of a cylinder which is circumscribed around the groove 53.

In Embodiment 1, an example is described in which the mold is attached to a vertical injection molding machine. Note, however, that Embodiment 1 is not limited to this and the mold can be attached to a horizontal injection molding machine.

<Production Method>

The following description will discuss a method for producing a tube 90 with use of the resin molding mold 1.

The method of Embodiment 1 for producing a tube includes, as an injection molding step, a primary molding step (first step) and a secondary molding step (second step).

In the injection molding carried out in the production method of Embodiment 1, first, molten resin is obtained by heating a moldable material in an injection unit (not illustrated), as with in conventional injection molding. Next, the molten resin is injected into a clamped mold, and then the molten resin is cooled, and thus a molded product is obtained. As a material for injection molding, general thermoplastic resin can be used. Alternatively, it is possible to appropriately select from urethane resin, vinyl chloride resin, polyethylene resin, other thermoplastic elastomer resin, and the like by taking into consideration moldability, a mechanical characteristic demanded of a product, and the like.

In the descriptions below, differences from conventional injection molding will be mainly described in detail.

(Primary Molding Step)

In the primary molding step, the reinforcing member 93 and the core pin 4 serving as a slide core are placed in the cavity 51 of the first mold 50. In this case, the reinforcing member 93 is placed so as to be inserted in the groove 53, and the core pin 4 is arranged so that a central axis of the core pin 4 and a central axis of the cavity 51 become collinear.

Next, molten resin is injected into the cavity 51 of the first mold 50 in a state where the reinforcing member 93 and the core pin 4 are placed in the cavity 51 as above described. Subsequently, the molten resin is cooled and solidified, and thus a primary molded body is obtained in which the reinforcing member 93 is provided along an outer peripheral surface of a first resin layer (tubular resin) having a tubular shape. Note that, on a surface of the primary molded body, the reinforcing member 93 can be partially exposed in the outer peripheral surface of the first resin layer having a tubular shape or the reinforcing member 93 does not need to be partially exposed in the outer peripheral surface of the first resin layer.

In an injection step in the primary molding step, the molten resin is injected into the first mold 50 via the gate 13, and is thus poured from one end of the first mold 50 to another end of the first mold 50. In this case, injection pressure is applied to the reinforcing member 93 in a direction from one end of the first mold 50 to another end of the first mold 50. In injection molding using a conventional mold, the reinforcing member may be moved in the cavity due to influence of injection pressure.

On the other hand, in the primary molding step, the reinforcing member 93 is inserted in the groove 53, and it is therefore possible to restrict movement of the reinforcing member 93 due to influence of injection pressure. This makes it possible to obtain the primary molded body in which the reinforcing member 93 is appropriately provided at an intended position at which the reinforcing member 93 is to be placed on an outer side of the first resin layer.

Note that, although the primary molded body is not illustrated in a drawing, the primary molded body formed by the injection molding has an outer shape that corresponds to a shape of an inner wall of the first mold 50. That is, the outer shape of the primary molded body becomes similar to a shape illustrated in (d) of FIG. 4.

(Secondary Molding Step)

In the secondary molding step, the primary molded body and the core pin 4 serving as a slide core are placed in the cavity 81 of the second mold 80. In this case, the primary molded body and the core pin 4 are arranged so that central axes of the primary molded body and the core pin 4 and a central axis of the cavity 81 become collinear. Note that the core pin 4 itself which has been inserted to the cavity 51 in the primary molding step can also be used for the cavity 81 or alternatively another core pin can be used for the cavity 81.

In a case where the primary molded body is placed in the cavity 81, there is a gap between the primary molded body and the inner wall surface 82 of the second mold 80 because an inner diameter of the second mold 80 is larger than an inner diameter of the first mold 50.

Next, molten resin is injected into the cavity 81 in a state where the primary molded body and the core pin 4 are placed in the cavity 81 as above described. As already described, there is a gap between the inner wall surface 82 and the primary molded body, and therefore the primary molded body is to be covered (i.e., surrounded) with the molten resin by injecting the molten resin into the cavity 81.

Subsequently, the molten resin is solidified, and thus a second resin layer is formed outside the first resin layer so as to cover the reinforcing member 93 which has been exposed in the surface of the primary molded body. As such, it is possible to produce the tube 90 (see FIG. 3) in which the reinforcing member 93 is embedded in the wall section 91 by the primary molding step and the secondary molding step.

In the above description, the production method has been described in which the tube 90 is produced by using the first mold 50 in which the groove 53 is provided in the inner wall surface 52. Note, however, that the production method of Embodiment 1 is not limited to this and, in a case where it is unnecessary to consider restriction of positional displacement of the reinforcing member 93, it is possible to employ a first mold 50 in which no groove 53 is provided in an inner wall surface 52. Even in such a case, it is not necessary to carry out a step of putting a reinforcing member over a tubular resin unlike the production method of Patent Literature 1, and it is therefore possible to produce the tube 90 which includes the reinforcing member 93 in the wall section 91 with the simpler processes. Further, in the production method of Embodiment 1, the injection molding is carried out while the reinforcing member 93 is placed in the cavity 51 of the first mold 50, and therefore no gap is formed between the tubular resin and the reinforcing member 93. From this, an amount of the molten resin that is needed to cover the reinforcing member 93 in the secondary molding step is smaller than that of liquid silicone rubber which is needed in the production method of Patent Literature 1. This makes it possible to produce the tube 90 in which the reinforcing member 93 is embedded in the wall section 91, without excessively enlarging an outer diameter of the tube 90 with respect to an inner diameter of the tube 90.

<Cross Section of Tube>

In the above described production method, the first resin layer is formed in the primary molding step and the second resin layer is formed outside the first resin layer in the secondary molding step. Therefore, the wall section 91 of the tube 90 is made up of (i) the first resin layer which is an inner layer and (ii) the second resin layer which is an outer layer.

Moreover, the reinforcing member 93 is provided along a boundary between the first resin layer and the second resin layer. That is, in a cross section (i.e., the partial cross-sectional view taken along the line b-b in (c) of FIG. 3) of the tube 90 taken along a plane including an axis direction of the tube 90, cross sections of the reinforcing member 93 are located at positions in the boundary between the first resin layer and the second resin layer.

As illustrated in (d) of FIG. 3, a protrusion which corresponds to the groove 53 in the inner wall surface 52 of the first mold 50 is provided on a surface of the primary molded body which has been obtained in the primary molding step, although the first resin layer may not completely cover an outer surface of the reinforcing member 93. Subsequently, the second resin layer is formed around the primary molded body in the secondary molding step, and therefore a recessed part corresponding to the protrusion is formed in the second resin layer which covers the protrusion corresponding to the groove 53. From this, (i) a part of the first resin layer, which part is around the cross section of the reinforcing member 93, is thicker than other parts of the first resin layer, (ii) a part of the second resin layer, which part is around the cross section of the reinforcing member 93, is thinner than other parts of the second resin layer, and, (iii) in the radial direction, a sum of the thickness of the part of the first resin layer, which part is around the cross section of the reinforcing member 93, and the thickness of the part of the second resin layer, which part is around the cross section of the reinforcing member 93, is equal to a thickness of the wall section 91.

Note that the first resin layer and the second resin layer can be made of identical resin materials or can be made of respective different resin materials which are compatible with each other.

Embodiment 2

Figure 6:
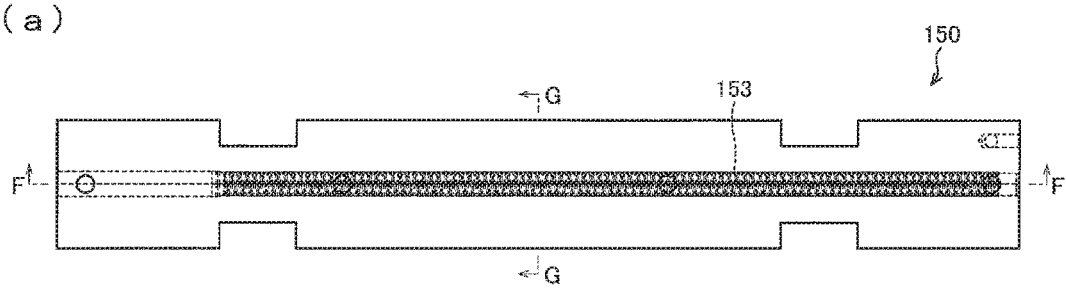
FIG. 6 is a view schematically illustrating a first mold in accordance with Embodiment 2 of the present invention. (a) of FIG. 6 is a plan view, (b) of FIG. 6 is a cross-sectional view taken along the line F-F in (a) of FIG. 6, (c) of FIG. 6 is a cross-sectional view taken along the line G-G in (a) of FIG. 6, and (d) of FIG. 6 is an enlarged view illustrating a part H in (b) of FIG. 6.
Figure 6:
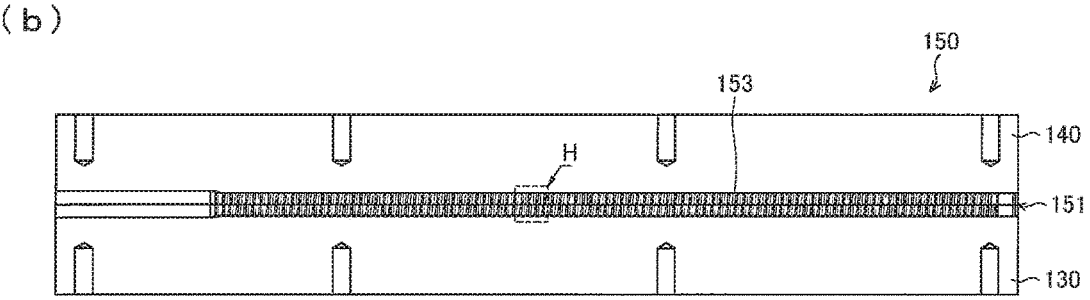
Figure 6:
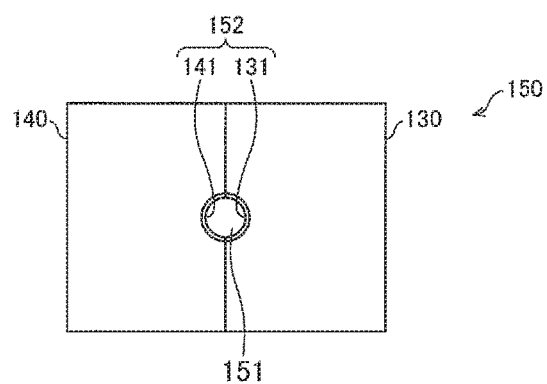
Figure 6:
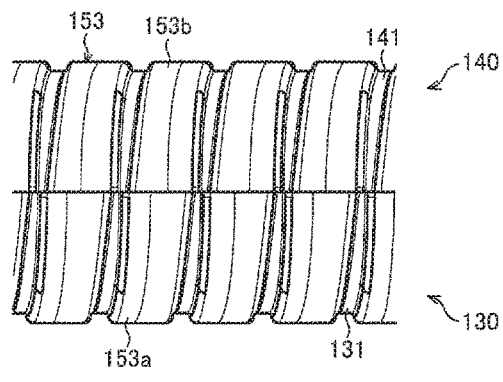

The following description will discuss, with reference to FIG. 6, details of a method for producing a tube, and a mold in accordance with an embodiment of the present invention. For convenience of explanation, identical reference numerals are given to constituent members identical to those described in Embodiment 1, and such constituent members will not be repeatedly described.

<Mold>

The following description will discuss a resin molding mold 1 which can be suitably used to produce a tube 90 illustrated in FIG. 3. The resin molding mold 1 of Embodiment 2 includes a first mold 150 and a second mold 80.

FIG. 6 is a view schematically illustrating the first mold 150 in accordance with Embodiment 2. (a) of FIG. 6 is a plan view, (b) of FIG. 6 is a cross-sectional view taken along the line F-F in (a) of FIG. 6, (c) of FIG. 6 is a cross-sectional view taken along the line G-G in (a) of FIG. 6, and (d) of FIG. 6 is an enlarged view illustrating a part H in (b) of FIG. 6. For explanation, (a) of FIG. 6 illustrates a groove which is provided in an inner wall surface of the first mold 150.

As illustrated in (c) of FIG. 6, by clamping a lower mold 130 for primary molding and an upper mold 140 for primary molding, a cavity 151 having a substantially cylindrical shape is formed in the first mold 150. Moreover, an inner wall surface 152 of the first mold 150 includes an inner wall surface 131 of the lower mold 130 for primary molding and an inner wall surface 141 of the upper mold 140 for primary molding.

In each of the inner wall surface 131 and the inner wall surface 141, a groove 153 corresponding to a shape of the reinforcing member 93 is provided. That is, as illustrated in (d) of FIG. 6, a groove 153a which is a part of the groove 153 is provided in the inner wall surface 131, and a groove 153b which is a part of the groove 153 is provided in the inner wall surface 141. When the lower mold 130 for primary molding and the upper mold 140 for primary molding are clamped, the grooves 153a and 153b which are respectively provided in the inner wall surface 131 and the inner wall surface 141 are combined into the groove 153 which is provided in the inner wall surface 152 of the first mold 150 and corresponds to a spiral shape of the reinforcing member 93.

With regard to a width of the groove 153 which width is parallel to a central axis direction of the cavity 151 and a width of the groove 53 which width is parallel to a central axis direction of the cavity 51 in the first mold 50, the width of the groove 153 is greater than the width of the groove 53. Specifically, the groove 153 is wide to an extent that the reinforcing member 93 can move in an internal space of the groove 153 in the central axis direction of the cavity 151. With the configuration, when the reinforcing member 93 is placed in the groove 153, a gap is formed between the reinforcing member 93 and a wall surface of the groove 153.

<Production Method>
(Primary Molding Step)

In a primary molding step, the reinforcing member 93 and a core pin 4 (see FIG. 1) are placed in the cavity 151 of the first mold 150, as with the production method of Embodiment 1. In this case, the reinforcing member 93 is placed so as to be inserted in the groove 153, and the core pin 4 is arranged so that a central axis of the core pin 4 and a central axis of the cavity 151 become collinear.

Next, molten resin is injected into the cavity 151 of the first mold 150 in a state where the reinforcing member 93 and the core pin 4 are placed in the cavity 151 as above described.

In this case, in the primary molding step, the reinforcing member 93 is inserted in the groove 153, and it is therefore possible to restrict movement of the reinforcing member 93 due to influence of injection pressure. Moreover, when the reinforcing member 93 is placed in the groove 153, a gap is formed between the reinforcing member 93 and the wall surface of the groove 153, and accordingly the molten resin flows into the gap.

Subsequently, the molten resin is solidified, and thus a primary molded body is obtained in which the reinforcing member 93 is provided along an outer peripheral surface of a first resin layer (tubular resin) having a tubular shape. Here, the molten resin is solidified in a state where the gap between the reinforcing member 93 and the wall surface of the groove 153 is filled with the molten resin, and therefore a protrusion which is made of the solidified resin and corresponds to a shape of the gap in the groove 153 is formed around the reinforcing member 93.

(Secondary Molding Step)

In a secondary molding step, the primary molded body and the core pin 4 are placed in a cavity of the second mold 80, as with the production method of Embodiment 1. In this case, the primary molded body and the core pin 4 are arranged so that central axes of the primary molded body and the core pin 4 and a central axis of the cavity 81 become collinear.

Next, molten resin is injected into the cavity 81 in a state where the primary molded body and the core pin 4 are placed in the cavity 81 as above described.

In this case, in the primary molded body, the protrusion which is made of the solidified resin is provided around the reinforcing member 93, and therefore the protrusion serves as a wall for restricting movement of the reinforcing member 93. From this, even in a case where the groove 153 is shallow to an extent that about a half of the reinforcing member 93 is inserted in the groove 153, it is possible to obtain the tube in which the reinforcing member is provided at an intended position at which the reinforcing member 93 is to be placed.

Moreover, as with the production method of Embodiment 1, there is a gap between an inner wall surface 82 (see (c) of FIG. 5) and the primary molded body, and therefore the primary molded body is to be covered (i.e., surrounded) with the molten resin by injecting the molten resin into the cavity 81.

Subsequently, the molten resin is solidified, and thus a second resin layer is formed outside the first resin layer so as to cover the reinforcing member 93 which has been exposed in the surface of the primary molded body. As such, it is possible to produce a tube 90 in which the reinforcing member 93 is embedded in the wall section 91 by the primary molding step and the secondary molding step.

According to the production method, in the primary molding step, the reinforcing member 93 is inserted in the groove. Therefore, even in a case where molten resin is injected into the first mold 150 with high injection pressure, it is possible to restrict movement of the reinforcing member 93 due to influence of injection pressure. Further, the protrusion is provided on the surface of the primary molded body, and the protrusion serves, in the secondary molding step, as a wall for restricting movement of the reinforcing member 93 in the axis direction of the primary molded body.

As such, in the primary molding step, positional displacement of the reinforcing member 93 due to injection pressure is restricted by the groove 153 and further, in the secondary molding step, positional displacement of the reinforcing member 93 due to injection pressure is restricted by the protrusion which is provided along the reinforcing member 93. This makes it possible to produce the tube 90 in which a part to be reinforced is reinforced by the reinforcing member 93 that is provided at the intended position with higher accuracy, and thus the tube which is hardly bent in a folded manner can be produced.

<Modification Example>

Note that it is possible that molten resin is injected, in the primary molding step, into the cavity 151 from one end side in a direction in which the reinforcing member 93 having a spiral shape extends, and molten resin is injected, in the secondary molding step, into the cavity 81 from another end side. Specifically, it is possible to employ the following configuration: i.e., in the primary molding step, molten resin is injected into the cavity 151 from an end on a Y side indicated in (d) of FIG. 6 and, in the secondary molding step, molten resin is injected into the cavity 81 from an end on a Y' side indicated in (d) of FIG. 6.

In this case, in the primary molding step, the reinforcing member 93 is subjected to injection pressure from the end on the Y side to the end on the Y' side, and accordingly moves from an end of the groove 153 on the Y side to an end of the groove 153 on the Y' side. Then, further movement of the reinforcing member 93 is restricted by a wall surface of the groove 153 on the Y' side. As a result, the reinforcing member 93 is placed at the end in the groove 153 on the Y' side, and therefore molten resin flows into a gap between the reinforcing member 93 and the end of the groove 153 on the Y side, and a protrusion made of solidified resin is formed on the Y side viewed from the reinforcing member 93.

In the subsequent secondary molding step, molten resin is injected into the cavity 81 from the end on the Y' side. In this case, the protrusion made of solidified resin is provided on the Y side viewed from the reinforcing member 93, and therefore movement of the reinforcing member 93 to the Y side is restricted by the protrusion.

This makes it possible to produce the tube 90 in which a part to be reinforced is reinforced by the reinforcing member 93 that is provided at the intended position with higher accuracy, and thus the tube 90 which is hardly bent in a folded manner can be produced.

<Cross Section of Tube>

In the above described production method, the first resin layer is formed in the primary molding step and the second resin layer is formed outside the first resin layer in the secondary molding step, as with the production method of Embodiment 1. Therefore, as early described with reference to FIG. 3, the wall section 91 of the tube 90 is made up of (i) the first resin layer which is an inner layer and (ii) the second resin layer which is an outer layer.

Moreover, the reinforcing member 93 is provided along a boundary between the first resin layer and the second resin layer. That is, in a cross section (i.e., the partial cross-sectional view taken along the line b-b in (c) of FIG. 3) of the tube 90 taken along a plane including an axis direction of the tube 90, cross sections of the reinforcing member 93 are located at positions in the boundary between the first resin layer and the second resin layer.

As indicated by dashed dotted lines in (d) of FIG. 3, a protrusion which corresponds to the groove 153 in the inner wall surface 152 of the first mold 150 is provided on a surface of the primary molded body which has been obtained in the primary molding step, although the first resin layer may not completely cover an outer surface of the reinforcing member 93. The protrusion corresponding to the groove 153 is wider than the protrusion corresponding to the groove 53.

Subsequently, the second resin layer is formed around the primary molded body in the secondary molding step, and therefore a recessed part that (i) corresponds to the protrusion and (ii) is wider than that in Embodiment 1 is formed in the second resin layer which covers the protrusion corresponding to the groove 153. From this, in a range broader than that of Embodiment 1, (i) a part of the first resin layer, which part is around the cross section of the reinforcing member 93, is thicker than other parts of the first resin layer and (ii) a part of the second resin layer, which part is around the cross section of the reinforcing member 93, is thinner than other parts of the second resin layer.

Embodiment 3

Figure 7:
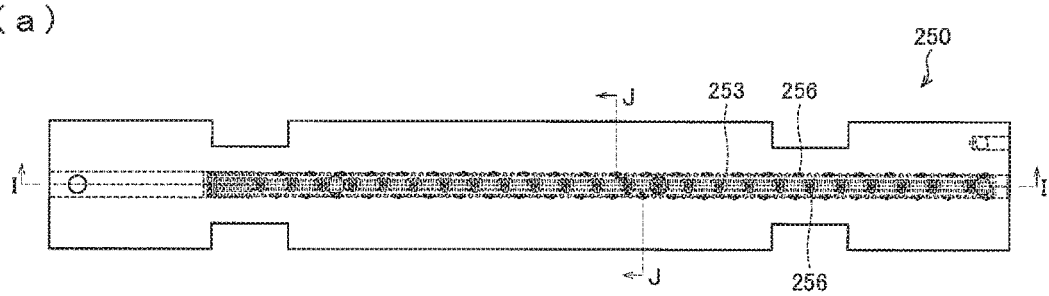
FIG. 7 is a view schematically illustrating a first mold in accordance with Embodiment 3 of the present invention. (a) of FIG. 7 is a plan view, (b) of FIG. 7 is a cross-sectional view taken along the line I-I in (a) of FIG. 7, (c) of FIG. 7 is a cross-sectional view taken along the line J-J in (a) of FIG. 7, and (d) of FIG. 7 is an enlarged view illustrating a part K in (b) of FIG. 7.
Figure 7:
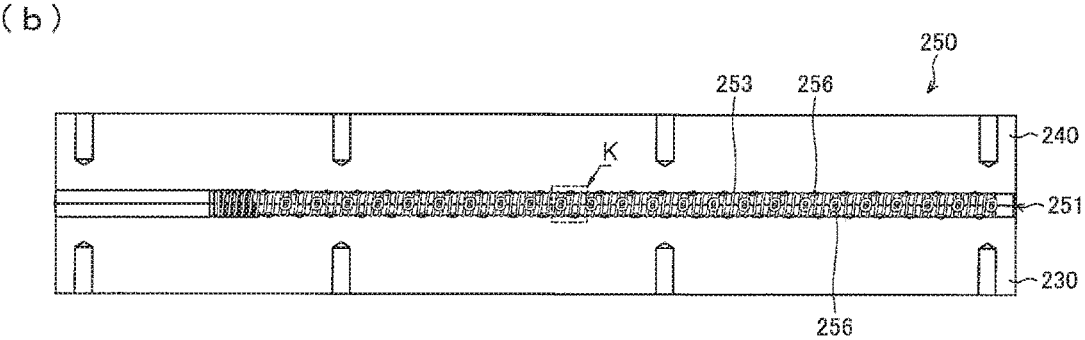
Figure 7:
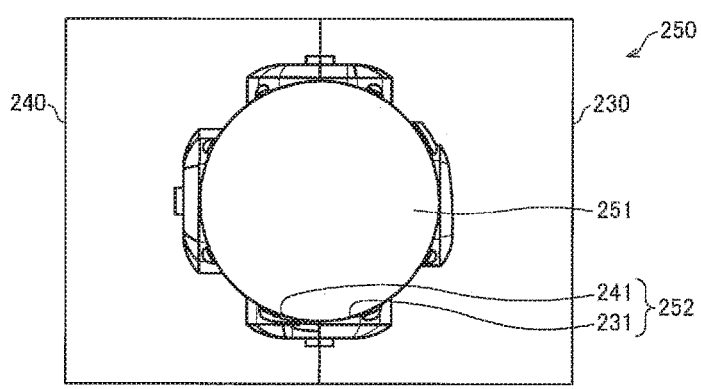
Figure 7:
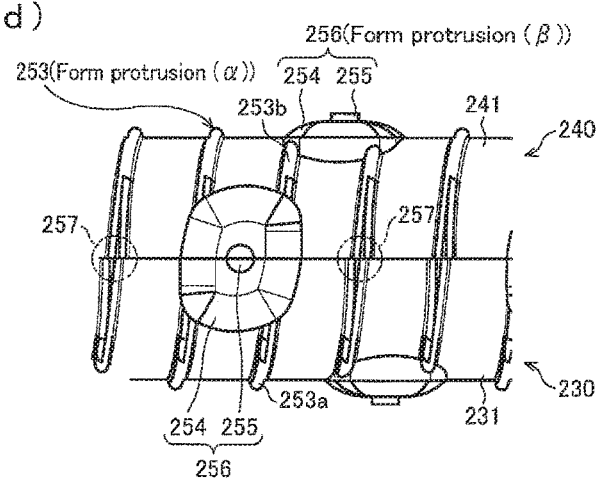

The following description will discuss, with reference to FIG. 7, details of a method for producing a tube, and a mold in accordance with an embodiment of the present invention. For convenience of explanation, identical reference numerals are given to constituent members identical to those described in Embodiments 1 and 2, and such constituent members will not be repeatedly described.

<Mold>

The following description will discuss a resin molding mold 1 which can be suitably used to produce a tube 90. The resin molding mold 1 of Embodiment 3 includes a first mold 250 and a second mold 80.

FIG. 7 is a view schematically illustrating the first mold 250 in accordance with Embodiment 3. (a) of FIG. 7 is a plan view, (b) of FIG. 7 is a cross-sectional view taken along the line I-I in (a) of FIG. 7, (c) of FIG. 7 is a cross-sectional view taken along the line J-J in (a) of FIG. 7, and (d) of FIG. 7 is an enlarged view illustrating a part K in (b) of FIG. 7. For explanation, (a) of FIG. 7 illustrates a groove which is provided in an inner wall surface of the first mold 250. Moreover, for explanation, (c) of FIG. 7 illustrates enlarged configurations of the constituent members.

As illustrated in (c) of FIG. 7, by clamping a lower mold 230 for primary molding and an upper mold 240 for primary molding, a cavity 251 having a substantially cylindrical shape is formed in the first mold 250. Moreover, an inner wall surface 252 of the first mold 250 includes an inner wall surface 231 of the lower mold 230 for primary molding and an inner wall surface 241 of the upper mold 240 for primary molding.

In each of the inner wall surface 231 and the inner wall surface 241, a groove corresponding to a shape of the reinforcing member 93 is provided, as with Embodiments1 and 2. When clamping is carried out, grooves 253a and 253b which are respectively provided in the inner wall surface 231 and the inner wall surface 241 are combined into a groove 253 which is provided in the inner wall surface 252 of the first mold 250 and corresponds to a spiral shape of the reinforcing member 93.

In the inner wall surface 252 of the first mold 250, a hole-like recessed part 256 is further provided. The hole-like recessed part 256 is provided so as to include at least part of a region located between adjacent portions of the groove 253.

The hole-like recessed part 256 is deeper than the groove 253. Moreover, the hole-like recessed part 256 includes a first hole-like recessed part 254 and a second hole-like recessed part 255 that is provided at a part of a bottom surface of the first hole-like recessed part 254.

The hole-like recessed part 256 can be provided within a space between adjacent portions of the groove 253. Alternatively, the hole-like recessed part 256 can be provided so as to cover (i.e., extend across) at least two adjacent portions of the groove 253.

Moreover, as already described, the groove can have a shape obtained by arbitrarily combining a spiral shape, a ring shape, and a wide-ring shape. That is, the hole-like recessed part can be provided so as to include at least part of a region between adjacent sections which are arbitrarily selected from (i) a spiral section corresponding to one turn of a spiral-shaped groove, (ii) a ring-shaped section corresponding to one of ring-shaped grooves, and (iii) a wide-ring-shaped section corresponding to one of wide-ring-shaped grooves.

Here, as illustrated in (d) of FIG. 7, in a case where the hole-like recessed part 256 is provided so as to cover two or more adjacent portions of the groove 253, the groove 253 is interrupted by the hole-like recessed part 256 in the inner wall surface 252. Even in such a case, the hole-like recessed part 256 is assumed to be provided so as to include at least part of a region located between adjacent portions of the groove 253.

The groove 253 has a spiral shape which is formed by a plurality of turns of spiral sections each of which is one turn of the spiral. Therefore, as is clear from the cross-sectional view illustrated in (d) of FIG. 7, the groove 253 includes a plurality of intersections 257 that intersect with a line which is on the inner wall surface 252 and is parallel to a central axis of the cavity 251. Further, the hole-like recessed part 256 is provided so as to at least include a region located between adjacent ones of the plurality of intersections 257.

A size of the second hole-like recessed part 255 in a plan view is preferably small and is preferably, for example, a size of 1 mm×1 mm. Note that, in Embodiment 3, the second hole-like recessed part 255 is not an essential element in the first mold 250. A merit of providing the second hole-like recessed part 255 will be described later.

Note that, in a case where a tube is produced in which a reinforcing member having a ring shape is embedded in a wall section, the first mold 250 of the resin molding mold 1 can be a mold in which (i) ring-shaped grooves each of which is closed are provided in the inner wall surface 252 and (ii) a hole-like recessed part is provided between every adjacent two of the ring-shaped grooves.

As illustrated in (b) and (d) of FIG. 7, a plurality of hole-like recessed parts 256 are discretely (preferably regularly) provided in the inner wall surface 252 of the first mold 250 along one of a plurality of lines parallel to the axis direction of the cavity 251. Further, a plurality of other hole-like recessed parts 256 are discretely provided along other one(s) of the plurality of lines. The number of the other one(s) of the plurality of lines is preferably 2 or more, and it is more preferable that the plurality of lines are arranged equiangularly on a circumference (i.e., on the inner wall surface 252) of the cavity 251, relative to a center of the cavity 251.

<Production Method>
(Primary Molding Step)

In a primary molding step, the reinforcing member 93 and a core pin 4 (see FIG. 1) are placed in the cavity 251 of the first mold 250, as with the production method of Embodiment 1. Next, molten resin is injected into the cavity 251 of the first mold 250 in a state where the reinforcing member 93 and the core pin 4 are placed in the cavity 251 as above described. In this case, the molten resin flows into the hole-like recessed part 256 that is provided in the inner wall surface 252.

Subsequently, the molten resin is solidified, and thus a primary molded body is obtained which includes (i) a first resin layer (tubular resin) that has a tubular shape and has a protrusion corresponding to the hole-like recessed part 256 and (ii) the reinforcing member 93 that is provided along an outer peripheral surface of the first resin layer.

Further, the hole-like recessed part 256 is provided between adjacent ones of the intersections 257, and therefore the protrusion is provided between two intersections at which the reinforcing member 93 having the spiral shape intersects with a line parallel to the central axis of the primary molded body. In other words, the protrusion is provided between two turns of spiral sections. Moreover, since the hole-like recessed part 256 is deeper than the groove 253, a peak of the protrusion on the surface of the primary molded body is positioned so as to protrude to an outer side than the outer peripheral surface of the reinforcing member 93.

Note that, in a case where the hole-like recessed part 256 of the first mold 250 is provided so as to overlap with two or more adjacent portions of the groove 253, it is possible to obtain a primary molded body in which a protrusion is provided so as to cover successive two or more spiral sections. Alternatively, in a case where the hole-like recessed part 256 of the first mold 250 is provided between adjacent two portions of the groove 253, it is possible to obtain a primary molded body in which a protrusion is provided between successive two turns of spiral sections.

(Secondary Molding Step)

In a secondary molding step, the primary molded body and the core pin 4 are placed in a cavity of the second mold 80, as with the production method of Embodiment 1. Next, molten resin is injected into the cavity 81 of the second mold 80 in a state where the primary molded body and the core pin 4 are placed in the cavity 81 as above described.

Subsequently, the molten resin is solidified, and thus a second resin layer is formed outside the first resin layer so as to cover the reinforcing member 93 which has been exposed in the surface of the primary molded body. As such, it is possible to produce a tube 90 in which the reinforcing member 93 is embedded in the wall section 91 by the primary molding step and the secondary molding step.

In an injection step in the secondary molding step, the molten resin is poured from one end of the second mold 80, at which one end a gate 13 is provided, to another end of the second mold 80. In this case, injection pressure is applied to the reinforcing member 93 in a direction from one end of the second mold 80 to another end of the second mold 80. In injection molding using a conventional mold, the reinforcing member may be moved in the cavity by receiving injection pressure of the molten resin.

On the other hand, according to the secondary molding step, the protrusion is provided between two turns of spiral sections which are included in the reinforcing member 93. Therefore, movement of the reinforcing member 93 in the axis direction of the primary molded body is restricted by the protrusion, and it is possible to restrict movement of the reinforcing member 93 due to influence of injection pressure.

As such, in the primary molding step, positional displacement of the reinforcing member 93 due to injection pressure is restricted by the groove 253 and further, in the secondary molding step, positional displacement of the reinforcing member 93 due to injection pressure is restricted by the protrusion which is provided between the spiral sections of the reinforcing member 93. This makes it possible to produce the tube 90 in which a part to be reinforced is reinforced by the reinforcing member 93 that is provided at the intended position with high accuracy, and thus the tube 90 which is hardly bent in a folded manner can be produced.

Further, according to the production method of Embodiment 3, when the primary molded body is placed in the cavity 81 of the second mold 80, the protrusion makes contact with the inner wall surface 82 of the second mold 80, and this reduces decentering of the primary molded body in the cavity 81. From this, in a longitudinal direction of the second mold 80, it is possible to enhance uniformity of a distance between the inner wall surface 82 of the second mold 80 and the surface of the primary molded body, and it is consequently possible to produce the tube 90 in which, in the longitudinal direction, uniformity in thickness of the wall section is improved.

As above described, since the protrusion for reducing decentering of the primary molded body in the cavity 81 is provided in the primary molded body, an injection direction of the molten resin in the secondary molding step can be a direction from a base part of the core pin 4 to a tip of the core pin 4 or, conversely, a direction from the tip of the core pin 4 to the base part. This is because of the following reason: that is, in a case where the injection direction from the tip to the base part of the core pin 4 is employed in a mode in which the protrusion is not provided in the primary molded body, decentering of the primary molded body easily occurs, whereas, in a mode in which the protrusion is provided in the primary molded body, the protrusion makes contact with the inner wall surface 82 of the second mold 80 and therefore decentering of the primary molded body hardly occurs.

In a case where the injection molding of the secondary molding step is carried out in a state where the protrusion is making contact with the inner wall surface 82 of the second mold 80, injected molten resin does not reach an upper surface of the protrusion, and therefore the upper surface of the protrusion is not covered with the molten resin. As a result, an exposed part (corresponding to the protrusion) in which the primary molded body is exposed and a covered part (corresponding to parts other than the protrusion) which is covered with the molten resin in the injection step of the secondary molding step are formed in the surface of the tube 90, and this may impair an appearance of the tube 90.

However, since the first mold 250 has the second hole-like recessed part 255, the protrusion has a lower protrusion which corresponds to the first hole-like recessed part 254 and an upper protrusion which corresponds to the second hole-like recessed part 255. The second hole-like recessed part 255 is provided at a part of the bottom surface of the first hole-like recessed part 254, and therefore the upper protrusion which is smaller in size is provided at a part of an upper surface of the lower protrusion. Therefore, an area of an upper surface of the upper protrusion is smaller than an area of the upper surface of the lower protrusion without the upper protrusion. As a result, an area of a part of the primary molded body which part makes contact with the inner wall surface 82 of the second mold 80 becomes smaller, as compared with a case where the protrusion has no upper protrusion. From this, a boundary line between an exposed part and a covered part becomes a small circle, and this makes it difficult to visually recognize the boundary line in the surface of the tube 90. As such, in a case where the second hole-like recessed part 255 is provided in the first mold 250, it is possible to improve the appearance of the tube 90, as compared with a case where the second hole-like recessed part 255 is not provided.

In the above description, the configuration has been described in which the hole-like recessed part 256 has the first hole-like recessed part 254 and the second hole-like recessed part 255. Note, however, that the configuration of the hole-like recessed part 256 is not limited to this.

The hole-like recessed part 256 does not need to include the second hole-like recessed part 255, provided that an area of its bottom surface is smaller than an area of its opening. For example, the hole-like recessed part 256 can have a shape such as a cone/pyramid shape or a dome shape in which a width decreases toward its bottom. From this, the protrusion provided in the primary molded body has a shape tapering toward the tip. This makes it possible to reduce an area of a part of the primary molded body which part makes contact with the inner wall surface 82 of the second mold 80, and this accordingly makes it difficult to visually recognize the boundary line in the surface of the tube 90. As such, in the aspect in which an area of the bottom surface of the hole-like recessed part 256 is smaller than an opening area of the hole-like recessed part 256, it is possible to improve the appearance of the tube 90, as compared with an aspect in which the area of the bottom surface of the hole-like recessed part 256 is equal to the opening area of the hole-like recessed part 256.

<Cross Section of Tube>

In the above described production method, the first resin layer is formed in the primary molding step and the second resin layer is formed outside the first resin layer in the secondary molding step. Therefore, as early described with reference to FIG. 3, the wall section 91 of the tube 90 is made up of (i) the first resin layer which is an inner layer and (ii) the second resin layer which is an outer layer.

Moreover, the reinforcing member 93 is provided along a boundary between the first resin layer and the second resin layer. That is, in a cross section (i.e., the partial cross-sectional view taken along the line b-b in (c) of FIG. 3) of the tube 90 taken along a plane including an axis direction of the tube 90, cross sections of the reinforcing member 93 are located at positions in the boundary between the first resin layer and the second resin layer.

A protrusion ($\alpha$) which corresponds to the groove 253 in the inner wall surface 252 of the first mold 250 and a protrusion ($\beta$) corresponding to the hole-like recessed part 256 are provided on a surface of the primary molded body which has been obtained in the primary molding step, although the first resin layer may not completely cover an outer surface of the reinforcing member 93. As above described, the protrusion ($\beta$) is provided between the spiral sections of the reinforcing member 93 having the spiral shape.

Subsequently, the second resin layer is formed around the primary molded body in the secondary molding step, and therefore a recessed part ($\alpha$) corresponding to the protrusion ($\alpha$) is formed in the second resin layer which covers the protrusion ($\alpha$) (see (e) of FIG. 3).

Further, a recessed part ($\beta$) corresponding to the protrusion ($\beta$) is formed (i) in the second resin layer which covers the protrusion ($\beta$) and (ii) between at least two spiral sections. That is, the boundary between the first resin layer and the second resin layer has a step that is formed in a part between successive two turns of spiral sections.

From this, in each of the recessed part ($\alpha$) and the recessed part ($\beta$), (i) a part of the first resin layer, which part is in each of the recessed part ($\alpha$) and the recessed part ($\beta$), is thicker than other parts of the first resin layer and (ii) a part of the second resin layer, which part is at each of the recessed part ($\alpha$) and the recessed part ($\beta$), is thinner than other parts of the second resin layer.

Embodiment 4

It is possible to employ resin molding that is carried out with a vacuum injection method, instead of the resin molding carried out with the injection molding method which is described in Embodiments 1 through 3. An example configuration of a vacuum injection device which is used to carry out vacuum injection is disclosed in Patent Literature 3 (Japanese Patent Application Publication Tokukai No. 2007-136713).

In the vacuum injection method, it is not necessary to inject molten resin into a mold with high pressure, unlike the injection molding method. It is therefore possible to reduce influence on the decentering of a core pin with respect to a central axis of a cavity in the mold.

As resin for use in vacuum injection, it is possible to employ two-part curing silicone resin, two-part curing urethane resin, or the like. A type of hardening reaction can be any of a condensation reaction type and an addition reaction type. It is preferable to employ two-part curing resin of an addition reaction type in which a reduction in weight caused by curing is small (i.e., a type in which a hardening reaction can be facilitated by heating).

<Mold>

It is possible to employ a mold whose structure is identical with any of those of the resin molding molds 1 used in injection moldings described in Embodiments 1 through 3.

<Production Method>

A tube production method of Embodiment 4 also includes, as a vacuum injection step, a primary molding step (first step) and a secondary molding step (second step), as with the foregoing injection molding step.

In the primary molding step, (i) the mold is placed in a vacuum chamber of the vacuum injection device, (ii) a main agent of two-part curing silicone rubber (resin), which main agent has been prepared in advance, and a curing agent are mixed, (iii) a resultant mixture is poured into a first mold (in which a core pin is being placed) from a sprue having a structure identical with that of the resin molding mold 1, and then (iv) pressure in the vacuum chamber is reduced to a vacuum state. Thus, defoaming is carried out to remove air contained in the resin which has been poured into the first mold. Next, resin that is enough to fill the cavity of the first mold is poured into the first mold, and then the vacuum chamber is opened to atmospheric pressure. This causes the resin to be pressed into and fill the cavity, and a hardening reaction proceeds, and thus a tube (primary molded body) having a predetermined shape can be produced. In order to facilitate the hardening reaction, it is possible to provide a warming device to the mold or the vacuum chamber so as to accelerate curing of the resin which has been poured. In this case, a heating temperature varies depending on a material of the resin and can be, for example, 60° C. to 80° C.

In the secondary molding step, the primary molded body and the core pin are placed in a cavity of a second mold having a structure identical with the resin molding mold 1, and vacuum injection is carried out in a manner similar to that described above. Thus, it is possible to produce a tube as an end molded product.

Note that this production method can also be applied to molding carried out with use of a thermosetting elastomer.

[Main Points]

In order to attain the object, a tube production method in accordance with an aspect of the present invention is a method for producing a tube which includes a wall section, a hollow section, and a reinforcing member, the reinforcing member being provided in the wall section and having a ring shape, a wide-ring shape, or a spiral shape, the method including the steps of: (a) forming a primary molded body, in which the reinforcing member is provided along an outer peripheral surface of a tubular resin, by carrying out resin molding while the reinforcing member and a core pin for forming the hollow section are placed in a cavity of a first mold; and (b) covering the reinforcing member by carrying out resin molding while the primary molded body is placed in a cavity of a second mold which has an inner diameter larger than an inner diameter of the first mold.

According to the production method, in the first step (a), the primary molded body can be formed in which the reinforcing member is provided along the outer peripheral surface of the tubular resin. After that, in the second step (b), it is possible to cover the reinforcing member that is provided along the outer peripheral surface of the tubular resin. From this, it is possible to produce the tube which (i) includes the reinforcing member that is provided in the wall section and has a ring shape or a spiral shape and (ii) is hardly bent in a folded manner.

Moreover, it is not necessary to carry out a step of putting a reinforcing member over a tubular resin unlike a conventional production method, and it is therefore possible to produce, with the simpler steps, the tube which includes the reinforcing member that is provided in the wall section and has a ring shape or a spiral shape.

Moreover, in the production method of Patent Literature 1, the silicone rubber tube is covered with the reinforcing body, and therefore the reinforcing body is designed to have an inner diameter which is larger than an outer diameter of the silicone rubber tube. As a result, there occurs a problem that an outer diameter of a produced tube becomes excessively larger than an inner diameter of the produced tube.

On the other hand, in the production method of the present invention, the resin molding is carried out while the reinforcing member is placed in the cavity of the first mold, and therefore no gap is formed between the tubular resin and the reinforcing member. As a result, the reinforcing member can be placed with high accuracy with respect to a radial direction of the primary molded body, and it is possible to omit redundant resin wall that is provided on an assumption of an extent to which the reinforcing member may be positionally displaced in the radial direction. From this, it is possible to produce the tube in which the reinforcing member is embedded in a thin wall section.

Note that, in the tube having the above described configuration, any tube-shaped reinforcing member can be suitably used, provided that the reinforcing member is an elastic body whose outline shape is a substantially tubular shape. For example, the reinforcing member can be in any of various forms such as a form of braided product, a form of knitted product, and a form of mesh-like product. Moreover, by adjusting a thickness and intervals of the reinforcing member, it is possible to control easiness in bending the tube and an oblateness of a cross section of the tube.

Moreover, the production method of Patent Literature 1 includes the injection step of injecting molten resin, with predetermined injection pressure, into the mold in which the reinforcing member (reinforcing body) is placed. In this case, the reinforcing member may be moved in the cavity by receiving the injection pressure of the molten resin. As a result, the reinforcing member may be provided while being displaced from an intended position at which the reinforcing member is to be placed, and it is therefore possible that a part to be reinforced is not reinforced and the tube is more likely to be bent in a folded manner. This problem can occur also in a case where the reinforcing member is made up of a single ring-shaped member.

Further, for example, in a case where a reinforcing member made of a plurality of rings is used or a reinforcing member having a spiral shape is used, there may be a case where the reinforcing member is not arranged at predetermined intervals and a part of the tube is more likely to be bent in a folded manner. In order to restrict movement of the reinforcing member due to injection of the molten resin, injection pressure may be reduced. However, in such a case, productivity of the tube decreases.

In view of this, in the tube production method in accordance with an aspect 2 of the present invention, it is possible that a groove is provided in an inner wall surface of the first mold, the groove corresponding to a shape of the reinforcing member; and in the step (a), the resin molding is carried out in a state where at least part of the reinforcing member is inserted in the groove.

According to the production method, at least part of the reinforcing member is inserted in the groove. Therefore, even in a case where molten resin is injected with high injection pressure into the first mold with use of an injection molding method as the resin molding method, the reinforcing member can remain in the position in which the groove is provided. That is, it is possible to restrict movement of the reinforcing member in an injection direction of the molten resin in the first mold due to influence of injection pressure. This makes it possible to obtain, in the first step (a), the primary molded body in which the reinforcing member is provided at the intended position along the outer peripheral surface of the tubular resin. As a result, it is possible to produce the tube in which a part to be reinforced is reinforced and which is hardly bent in a folded manner.

In a case where a vacuum injection method is used as the resin molding method, pressure applied to resin in injecting the resin into the first mold is lower, as compared with pressure in the injection molding method. Even so, it is still possible to bring about an effect of causing the reinforcing member to surely remain in the position in which the groove is provided.

In particular, in a case where the reinforcing member is (i) a reinforcing member having a spiral shape or (ii) a reinforcing member made of a plurality of rings or a plurality of wide rings, positions at which the reinforcing member is to be provided in an axis direction of the tube do not become nonuniform, and it is therefore possible to provide the reinforcing member having designed distribution. As a result, for example, it is possible to uniformize flexural property across the entire tube in the axis direction.

In the tube production method in accordance with an aspect 3 of the present invention, it is possible that the groove has (i) a spiral shape or (ii) a shape formed by a plurality of ring-shaped grooves or a plurality of wide-ring-shaped grooves which are arranged at regular intervals or at controlled irregular intervals in a direction parallel to a central axis of the cavity; the groove includes (i) a spiral section which corresponds to one turn of a spiral-shaped groove or (ii) a ring-shaped section which corresponds to one of the plurality of ring-shaped grooves or a wide-ring-shaped section which corresponds to one of the plurality of wide-ring-shaped grooves; a hole-like recessed part is further provided so that the hole-like recessed part includes at least part of a region located between adjacent sections selected from spiral sections, ring-shaped sections, and wide-ring-shaped sections; and the hole-like recessed part is deeper than the groove.

Here, a shape of the grooves can be a shape formed by arbitrarily combining the spiral shape, the ring shape, and the wide-ring shape.

According to the production method, in a resin introduction step in the resin molding of the first step (a), the molten resin flows in the hole-like recessed part that is provided in the inner wall surface of the first mold, and thus a first protrusion corresponding to the hole-like recessed part is formed on the surface of the primary molded body.

The hole-like recessed part is provided so as to include at least part of a region between adjacent ones of a spiral section, a ring-shaped section, and a wide-ring-shaped section. In other words, the hole-like recessed part is provided so as to include at least part of a region between arbitrarily selected adjacent ones of one turn of a spiral section, one ring-shaped section, and one wide-ring-shaped section. Therefore, the first protrusion corresponding to the hole-like recessed part is provided so as to include at least part of a region between arbitrarily selected adjacent ones of (i) a spiral member that corresponds to one turn of a reinforcing member that has a spiral shape, (ii) a reinforcing member which is a single ring, and (iii) a reinforcing member which is a single wide ring. Further, the hole-like recessed part is deeper than the groove in which the reinforcing member is inserted, and therefore a peak of the first protrusion on the surface of the primary molded body is positioned so as to protrude to an outer side than the outer peripheral surface of the reinforcing member.

Therefore, movement of the reinforcing member in the axis direction of the primary molded body is restricted by the first protrusion. From this, as above described, it is possible to obtain the primary molded body in which the reinforcing member is provided at an intended position at which the reinforcing member is to be provided, and it is possible, in a resin introduction step in resin molding of the second step (b), to restrict movement of the reinforcing member due to resin introduction pressure. This makes it possible to obtain the tube in which the reinforcing member is surely provided at the intended position. As a result, it is possible to produce the tube in which a part to be reinforced is reinforced and which is hardly bent in a folded manner.

Moreover, in order to attain the object, the mold in accordance with an aspect of the present invention is a mold for forming a tube which includes a wall section, a hollow section, and a reinforcing member, the reinforcing member being provided in the wall section and having a ring shape, a wide-ring shape, or a spiral shape, the mold including: a groove corresponding to a shape of the reinforcing member, the groove being provided in an inner wall surface that forms a cavity.

According to the configuration, resin is introduced into the cavity while the reinforcing member is inserted in the groove of the mold when a resin introduction step of resin molding such as injection molding or vacuum injection is carried out. It is therefore possible to restrict movement of the reinforcing member in an axis direction of the cavity.

From this, it is possible to obtain a molded body in which the reinforcing member is provided at the intended position along an outer peripheral surface of a tubular resin. Subsequently, the reinforcing member that is exposed in a surface of the molded body is covered, and it is thus possible to produce the tube in which a part to be reinforced is reinforced and which is hardly bent in a folded manner.

Moreover, according to the mold in accordance with an aspect 5 of the present invention, it is possible that the groove has (i) a spiral shape or (ii) a shape formed by a plurality of ring-shaped grooves or a plurality of wide-ring-shaped grooves which are arranged at regular intervals or at controlled irregular intervals in a direction parallel to a central axis of the cavity; the groove includes (i) a spiral section which corresponds to one turn of a spiral-shaped groove or (ii) a ring-shaped section which corresponds to one of the plurality of ring-shaped grooves or a wide-ring-shaped section which corresponds to one of the plurality of wide-ring-shaped grooves; the mold further includes a hole-like recessed part which is provided so as to include at least part of a region located between adjacent sections selected from spiral sections, ring-shaped sections, and wide-ring-shaped sections; and the hole-like recessed part is deeper than the groove.

As already described, the shape of the grooves can be a shape formed by arbitrarily combining the spiral shape, the ring shape, and the wide-ring shape.

According to the configuration, molten resin flows into the hole-like recessed part, and thus a first protrusion corresponding to the hole-like recessed part is formed on a surface of a molded body.

The hole-like recessed part is provided so as to include at least part of a region between adjacent ones of a spiral section, a ring-shaped section, and a wide-ring-shaped section. In other words, the hole-like recessed part is provided so as to include at least part of a region between arbitrarily selected adjacent ones of one turn of a spiral section, one ring-shaped section, and one wide-ring-shaped section. Therefore, the first protrusion corresponding to the hole-like recessed part is provided so as to include at least part of a region between arbitrarily selected adjacent ones of (i) a spiral member that corresponds to one turn of a reinforcing member that has a spiral shape, (ii) a reinforcing member which is a single ring, and (iii) a reinforcing member which is a single wide ring. Further, the hole-like recessed part is deeper than the groove in which the reinforcing member is inserted, and therefore a peak of the first protrusion on the surface of the primary molded body is positioned so as to protrude to an outer side than the outer peripheral surface of the reinforcing member.

Therefore, movement of the reinforcing member in the axis direction of the molded body is restricted by the first protrusion. From this, in a step of covering the reinforcing member that is exposed in the surface of the molded body, it is possible to restrict movement of the reinforcing member in the axis direction of the molded body, and this makes it possible to obtain the tube in which the reinforcing member is provided at the intended position. As a result, it is possible to produce the tube in which a part to be reinforced is reinforced and which is hardly bent in a folded manner.

According to the mold in accordance with an aspect 6 of the present invention, it is possible that the groove is wider than the reinforcing member; and in a case where the reinforcing member is placed in the groove, a gap is formed between the reinforcing member and a wall surface of the groove.

According to the configuration, in a case where resin molding is carried out in a state where the reinforcing member is inserted in the groove, the molten resin flows into the gap between the reinforcing member and the wall surface of the groove, and thus a protrusion corresponding to the gap is formed on the surface of the primary molded body.

In a resin introduction step in resin molding of the subsequent second step, resin is introduced into the mold for the second step. In this case, the reinforcing member receives introduction pressure but the protrusion corresponding to the gap functions as a wall for restricting movement of the reinforcing member. From this, even in a case where the groove is shallow to an extent that about a half of the reinforcing member is inserted in the groove, it is possible to obtain the tube in which the reinforcing member is provided at the intended position. As a result, it is possible to produce the tube in which a part to be reinforced is reinforced and which is hardly bent in a folded manner.

Moreover, in order to attain the object, the tube in accordance with an aspect of the present invention is a tube including: a wall section; a hollow section; a reinforcing member which is provided in the wall section and serves as at least one ring-shaped member, at least one wide-ring-shaped member, or at least one turn of a spiral-shaped member; a first resin layer; and a second resin layer which is provided on an outer side of the first resin layer, in a cross section of the tube taken along a plane including an axis direction of the tube, a cross section of the reinforcing member being located in a boundary between the first resin layer and the second resin layer, a part of the first resin layer, which part is around the cross section of the reinforcing member, being thicker than other parts of the first resin layer, and a part of the second resin layer, which part is around the cross section of the reinforcing member, being thinner than other parts of the second resin layer.

According to the configuration, in the cross section of the tube taken along the plane including the axis direction of the tube, the boundary between the first resin layer and the second resin layer has a step around the reinforcing member.

Therefore, the tube has a structure in which positional displacement of the reinforcing member is restricted by the step and the reinforcing member is provided at an intended position at which the reinforcing member is to be placed. As a result, it is possible to provide the tube in which a part to be reinforced is reinforced and which is hardly bent in a folded manner.

Moreover, according to the tube in accordance with an aspect 8 of the present invention, it is possible that the reinforcing member is (i) a plurality of ring-shaped members including the at least one ring-shaped member, (ii) a plurality of wide-ring-shaped members including the at least one wide-ring-shaped member, or (iii) a plurality of turns of the spiral-shaped member including the at least one turn of the spiral-shaped member; and, in the cross section of the tube, a part of the first resin layer, which part is between at least two adjacent cross sections of the reinforcing member, is thicker than other parts of the first resin layer, and a part of the second resin layer, which part is between the at least two adjacent cross sections of the reinforcing member, is thinner than other parts of the second resin layer.

According to the configuration, a part of the first resin layer, which part is between at least two adjacent cross sections of the reinforcing member, is thicker than other parts of the first resin layer, and a part of the second resin layer, which part is between the at least two adjacent cross sections of the reinforcing member, is thinner than other parts of the second resin layer. That is, the thickness of the first resin layer (or the second resin layer) varies between (i) a region that is located between the cross sections and (ii) the other region, and therefore a step is formed between the region and the other region.

According to the configuration, positional displacement of the reinforcing member is further restricted by the step in the tube, and thus the reinforcing member is surely provided at a position at which the reinforcing member is to be placed. As a result, it is possible to provide the tube in which a part to be reinforced is reinforced with higher accuracy and which is hardly bent in a folded manner.

The present invention is not limited to the embodiments, but can be altered by a skilled person in the art within the scope of the claims. An embodiment derived from a proper combination of technical means each disclosed in a different embodiment is also encompassed in the technical scope of the present invention.

INDUSTRIAL APPLICABILITY

The present invention can be used for a purpose of restraining a hollow section of a tube from becoming narrow by bending. For example, the present invention is applicable to a medical tube.

REFERENCE SIGNS LIST

4: Core pin
30: Lower mold for primary molding 50, 150, 250: First mold
51, 151, 251: Cavity
52, 152, 252: Inner wall surface
53, 153, 253: Groove
80: Second mold
81: Cavity
90: Tube
91: Wall section
92: Hollow section
93: Reinforcing member
256: Hole-like recessed part
257: Intersection

The invention claimed is:

1. A medical tube for insertion into a patient's body, the medical tube comprising:
    a wall section;
    a hollow section;
    a reinforcing member which is provided in the wall section and being formed as a spiral-shaped member;
    a first resin layer; and
    a second resin layer which is provided on an outer side of the first resin layer,
    in a cross section of the tube taken along a plane including an axis direction of the tube, a cross section of the reinforcing member being located in a boundary between the first resin layer and the second resin layer,
    a part of the first resin layer, which is arranged between the reinforcing member in the cross section of the tube, being thicker than other parts of the first resin layer, the part of the first resin layer being provided axially on a surface of the first resin layer at regular intervals so as to form a repeating pattern,
    wherein the medical tube is configured to be inserted into the patient's body, and
    the reinforcing member is at least partially embedded in the first resin layer.

2. The medical tube as set forth in claim 1, wherein:
    the reinforcing member is the spiral-shaped member; and
    in the cross section of the tube, the part of the first resin layer, which is between at least two adjacent cross sections of the reinforcing member, is thicker than other parts of the first resin layer, and a corresponding part of the second resin layer, which is between the at least two adjacent cross sections of the reinforcing member, is thinner than other parts of the second resin layer.

* * * * *